US011699422B2

(12) United States Patent
Dave et al.

(10) Patent No.: US 11,699,422 B2
(45) Date of Patent: Jul. 11, 2023

(54) ACTIVE ADAPTIVE NOISE AND VIBRATION CONTROL

(71) Applicant: CareFusion 303, Inc., San Diego, CA (US)

(72) Inventors: Jay Jyotindra Dave, Carlsbad, CA (US); Julio Cesar Gomes Pimentel, San Diego, CA (US); Matthew M. Miceli, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 129 days.

(21) Appl. No.: 17/318,969

(22) Filed: May 12, 2021

(65) Prior Publication Data
US 2021/0366457 A1    Nov. 25, 2021

Related U.S. Application Data

(60) Provisional application No. 63/027,867, filed on May 20, 2020.

(51) Int. Cl.
*G10K 11/16* (2006.01)

(52) U.S. Cl.
CPC .................................. *G10K 11/16* (2013.01)

(58) Field of Classification Search
CPC ............... G10K 11/16; G10K 11/1785; G10K 11/17873; G10K 2210/116
See application file for complete search history.

(56) References Cited

U.S. PATENT DOCUMENTS

| 5,548,653 | A | 8/1996 | Pla et al. |
| 2008/0110459 | A1 | 5/2008 | Farbarik |
| 2016/0199241 | A1 | 7/2016 | Rapoport |
| 2019/0073990 | A1 | 3/2019 | Moss et al. |
| 2019/0311706 | A1 | 10/2019 | MacLaughlin |
| 2020/0001469 | A1 | 1/2020 | Park |

FOREIGN PATENT DOCUMENTS

JP     2016171926 A    9/2016

OTHER PUBLICATIONS

International Preliminary Report on Patentability from the International Preliminary Examining Authority for Application No. PCT/US2021/033020, dated Aug. 5, 2022, 22 pages.
Written Opinion from the International Preliminary Examining Authority for Application No. PCT/US2021/033020, dated May 10, 2022, 8 pages.
International Search Report and Written Opinion for Application No. PCT/US2021/033020, dated Aug. 24, 2021, 17 pages.

*Primary Examiner* — David L Ton
(74) *Attorney, Agent, or Firm* — Morgan Lewis & Bockius LLP

(57) ABSTRACT

Methods and systems for actively and adaptively cancelling the noise and vibration generated by medical devices. A method includes receiving data from one or more sensors of a medical device. The method includes determining a signature signal for the medical device based at least on the data. The signature signal is a representation of one or more physical byproducts of the medical device, and one or more environmental conditions of a physical environment proximate to the medical device. The method incudes determining an inverted signal based on the signature signal, the inverted signal configured to mask the signature signal. The method includes generating a physical representation of the inverted signal by one or more electrical or electromechanical components of the medical device, and masking the signature signal with the inverted signal.

20 Claims, 8 Drawing Sheets

600

602
Receive data from one or more sensors of a medical device

604
Wherein the one or more sensors of the medical device include at least one of an accelerometer, displacement sensor, velocity sensor, sound sensors, sound transducers

606
Determine a signature signal for the medical device based at least on the data, wherein the signature signal is a representation of physical attributes of a physical environment proximate to the medical device including one or more physical byproducts of the medical device, and one or more environmental conditions of the physical environment proximate to the medical device

608
Wherein the signature signal includes at least one of an audio signal and/or vibration signal

610
Receive operation information from at least one or more motor controllers of the medical device and wherein the signature signal for the medical device is further based on the operational information

612
Wherein the operational information includes at least a voltage, frequency and/or current usage of one or more motors controlled by the one or more motor controllers

614
Receive, via user input, information about the physical environment proximate to the medical device and wherein the signature signal for the medical device is further based on the information

616
Wherein the information about the physical environment proximate to the medical device includes at least one of a number of other active medical devices and/or inactive medical devices proximate to the medical device, a location of the medical device, other non-medical devices proximate to the medical device, a number of patients proximate to the medical device, and/or a configuration of the medical device or other devices

Figure 6A

632-a
Determine respective signature signals for the medical device and the other medical device based at least on the data and the additional data

632-b
Determine respective inverted signals based on the respective signature signals, wherein the respective inverted signals are configured to cancel the respective signature signals,

632-c
Generate respective physical representations of the respective inverted signals by one or more respective electrical or electromechanical components of the medical device and the other medical device, wherein the respective physical representations of the respective inverted signals cancel respective physical attributes of the environment represented by the respective signature signals

634
After cancelling the physical attributes of the environment represented by the signature signal, storing at least the signature signal

636-a
Receive subsequent data from the one or more sensors of the medical device

636-b
Determine a subsequent signature signal for the medical device based on the subsequent data and a stored signature signal

636-c
Determine a subsequent inverted signal based on the subsequent signature signal, wherein the subsequent inverted signal is configured to cancel the subsequent signature signal

636-d
Generate a physical representation of the subsequent inverted signal by the one or more electrical or electromechanical components of the medical device, wherein the physical representation of the subsequent inverted signal cancels the physical attributes of the environment represented by the subsequent signature signal

Figure 6C

ACTIVE ADAPTIVE NOISE AND VIBRATION CONTROL

CROSS REFERENCE TO RELATED APPLICATIONS

This application is a nonprovisional of U.S. Provisional Application Ser. No. 63/027,867, entitled "ACTIVE ADAPTIVE NOISE AND VIBRATION CONTROL," filed on May 20, 2020, the entirety of which is incorporated herein by reference.

TECHNICAL FIELD

The present disclosure is generally related to active adaptive noise and vibration control. More specifically, the present disclosure relates to methods and systems of cancelling noise and/or vibrations generated by one or more medical devices.

BACKGROUND

Medical devices can create loud noises and strong vibrations that can annoy and/or disturb patients. As medical devices are operated at higher power levels, more frequently, and/or with other medical devices, the louder sounds and vibrations are generated. This may result in an uncomfortable and unpleasant experience for patients and/or medical practitioners. The vibrations and noise may also impact the functioning of a medical device such as by interfering with audio detection by the medical device or accelerating wear and tear on the medical device from the vibrations. As such, there is a need to improve the experience of patients that rely on medical devices for their health.

SUMMARY

In some implementations, a computer-implemented method includes receiving data from one or more sensors of a medical device. The method includes determining a signature signal for the medical device based at least on the data. The signature signal is a representation of physical attributes of a physical environment proximate to the medical device including: one or more physical byproducts of the medical device, and one or more environmental conditions of the physical environment proximate to the medical device. The method includes determining an inverted signal based on the signature signal, the inverted signal configured to cancel the signature signal. The method further includes generating a physical representation of the inverted signal by one or more electrical or electromechanical components of the medical device, wherein the physical representation of the inverted signal cancels the physical attributes of the environment represented by the signature signal.

In some implementations a system includes a memory storing instructions, and one or more processors coupled with the memory and configured to execute the instructions to cause the system to receive data from one or more sensors of a medical device. The instructions, when executed by the one or more processors, cause the system to determine a signature signal for the medical device based at least on the data. The signature signal is a representation of physical attributes of a physical environment proximate to the medical device including: one or more physical byproducts of the medical device, and one or more environmental conditions of the physical environment proximate to the medical device. The instructions, when executed by the one or more processors, cause the system to determine an inverted signal based on the signature signal, the inverted signal configured to cancel the signature signal. The instructions, when executed by the one or more processors, further cause the system to generate a physical representation of the inverted signal by one or more electrical or electromechanical components of the medical device, wherein the physical representation of the inverted signal cancels the physical attributes of the environment represented by the signature signal.

In further implementations, a non-transitory, computer-readable medium storing instructions which, when executed by a processor in a computer, cause the computer to perform a method, the method including receiving data from one or more sensors of a medical device. The method, performed by the computer, includes determining a signature signal for the medical device based on the data. The signature signal is a representation of physical attributes of a physical environment proximate to the medical device including: one or more physical byproducts of the medical device, and one or more environmental conditions of the physical environment proximate to the medical device. The method, performed by the computer, includes determining an inverted signal based on the signature signal, the inverted signal configured to cancel the signature signal. The method, performed by the computer, includes generating a physical representation of the inverted signal by one or more electrical or electromechanical components of the medical device, wherein the physical representation of the inverted signal cancels the physical attributes of the environment represented by the signature signal.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

FIGS. 6A-6C are flowcharts illustrating an example method for active adaptive noise and vibration control according to illustrative implementations.

DETAILED DESCRIPTION

Implementations as disclosed herein include an active adaptive noise and vibration control system that are configured to reduce or eliminate the vibrations and/or sounds generated by medical devices. The active adaptive noise and vibration control system is implemented in a server and/or in individual medical devices. Accordingly, implementations as disclosed herein provide active adaptive noise and vibration cancellation for medical devices to reduce or eliminate the sounds and/or vibrations that may disturb patients. Also, by providing active adaptive noise and vibration cancellation for medical devices, implementations as disclosed herein facilitate the use of multiple medical devices simultaneously without generating an uncomfortable environment, reducing the amount space to treat patients by enabling multiple devices to be operational in confined spaces (e.g., allowing for patient care areas to be used more efficiently).

Some additional advantages of the implementations consistent with the present disclosure include improved performance by reducing the magnitude of physical byproducts (e.g., sounds and/or vibrations) generated by medical devices operating in different configurations. In particular, medical devices can operate at higher power levels and/or (generally) louder configurations without creating additional disturbances for patients. Implementations as disclosed herein are suitable for a variety of scenarios and or situations where multiple medical devices can be active at a single time or when certain medical known to generate loud sounds and/or strong vibrations are active. Accordingly, reducing or eliminating sounds and/or vibrations generated by medical devices may resolve annoyances and discomforts to patients before they become uncomfortable and ensure proper continued operation of the medical devices.

Figure 1:
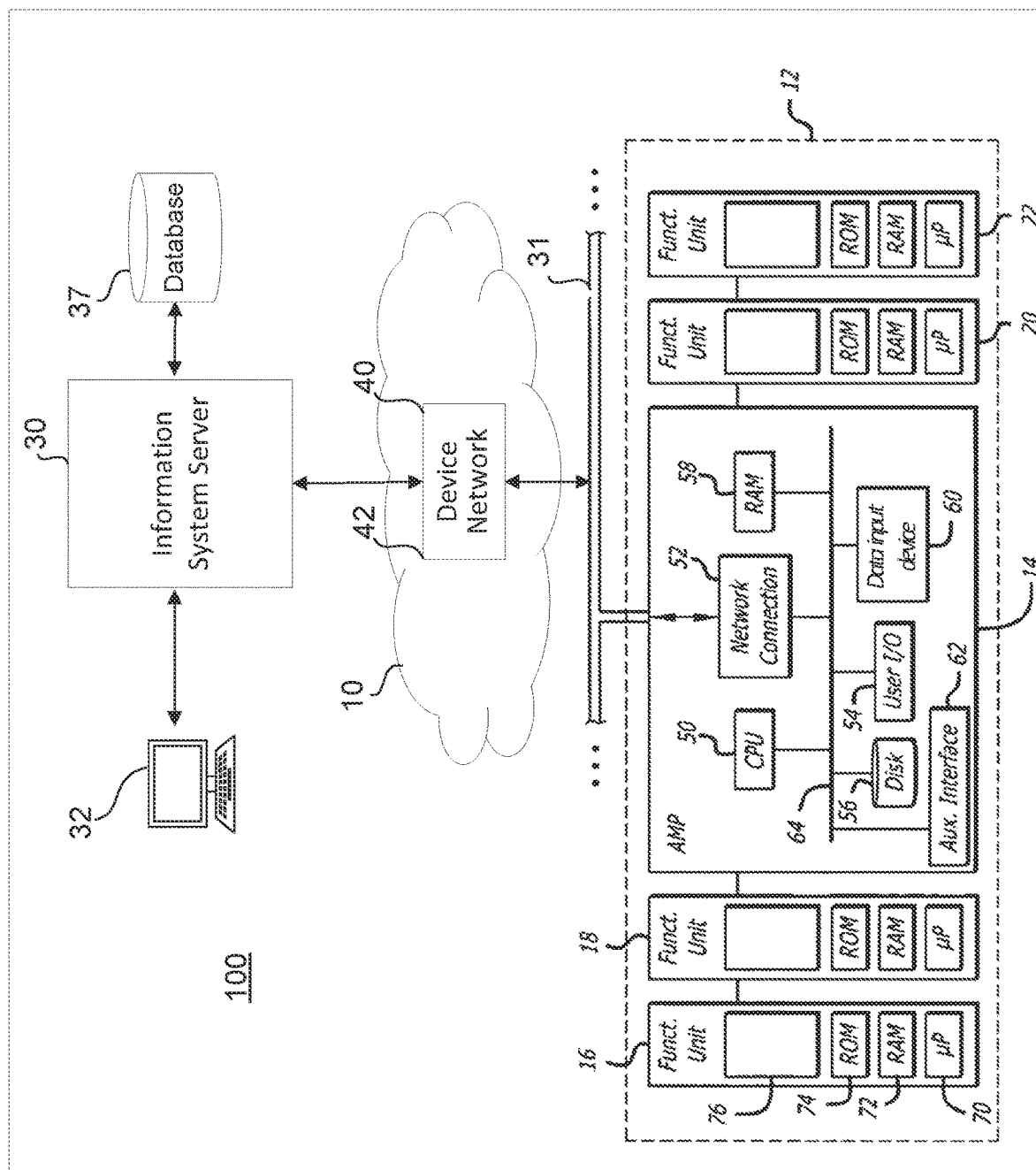
FIG. 1 depicts an example of an institutional patient care system of a healthcare organization, according to aspects of the subject technology.

FIG. 1 depicts an example of an institutional patient care system 100 of a healthcare organization, in accordance with some implementations. In FIG. 1, a patient care device (or "medical device" generally) 12 is connected to a hospital network 10. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each element 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 40 by which patient care devices 12 (and other devices) communicate in accordance with normal operations.

Additionally, institutional patient care system 100 may incorporate a separate information system server 30, the function of which will be described in more detail below. Moreover, although the information system server 30 is shown as a separate server, the functions and programming of the information system server 30 may be incorporated into another computer, if such is desired by engineers designing the institution's information system. Institutional patient care system 100 may further include one or multiple device terminals 32 for connecting and communicating with information system server 30. Device terminals 32 may include personal computers, personal data assistances, mobile devices such as laptops, tablet computers, augmented reality devices, or smartphones, configured with software for communications with information system server 30 via network 10.

Patient care device 12 comprises a system for providing patient care, such as that described in U.S. Pat. No. 5,713,856 to Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 16, 18, 20, 22. Interface unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20 and 22, and configured to communicate with controller 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor, an intracranial pressure monitor, or the like. Functional module 18, 20 and/or 22 may be a printer, scanner, bar code reader or any other peripheral input, output or input/output device.

Each functional module 16, 18, 20, 22 communicates directly or indirectly with interface unit 14, with interface unit 14 providing overall monitoring and control of device 12. Functional modules 16, 18, 20, 22 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 may include module-specific components 76, a microprocessor 70, a volatile memory 72 and a nonvolatile memory 74 for storing information. It should be noted that while four functional modules are shown in FIG. 1, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 16.

While each functional module may be capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

Patient care device 12 is capable of operating in several different modes, or personalities, with each personality defined by a configuration database. The configuration database may be a database 56 internal to patient care device, or an external database 37. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from a pharmacy server, admissions server, laboratory server, and the like.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in HIS server 30, decision support 48, remote data server 49, hospital department or unit stations 46, or within patient care device 12 itself.

Figure 2:
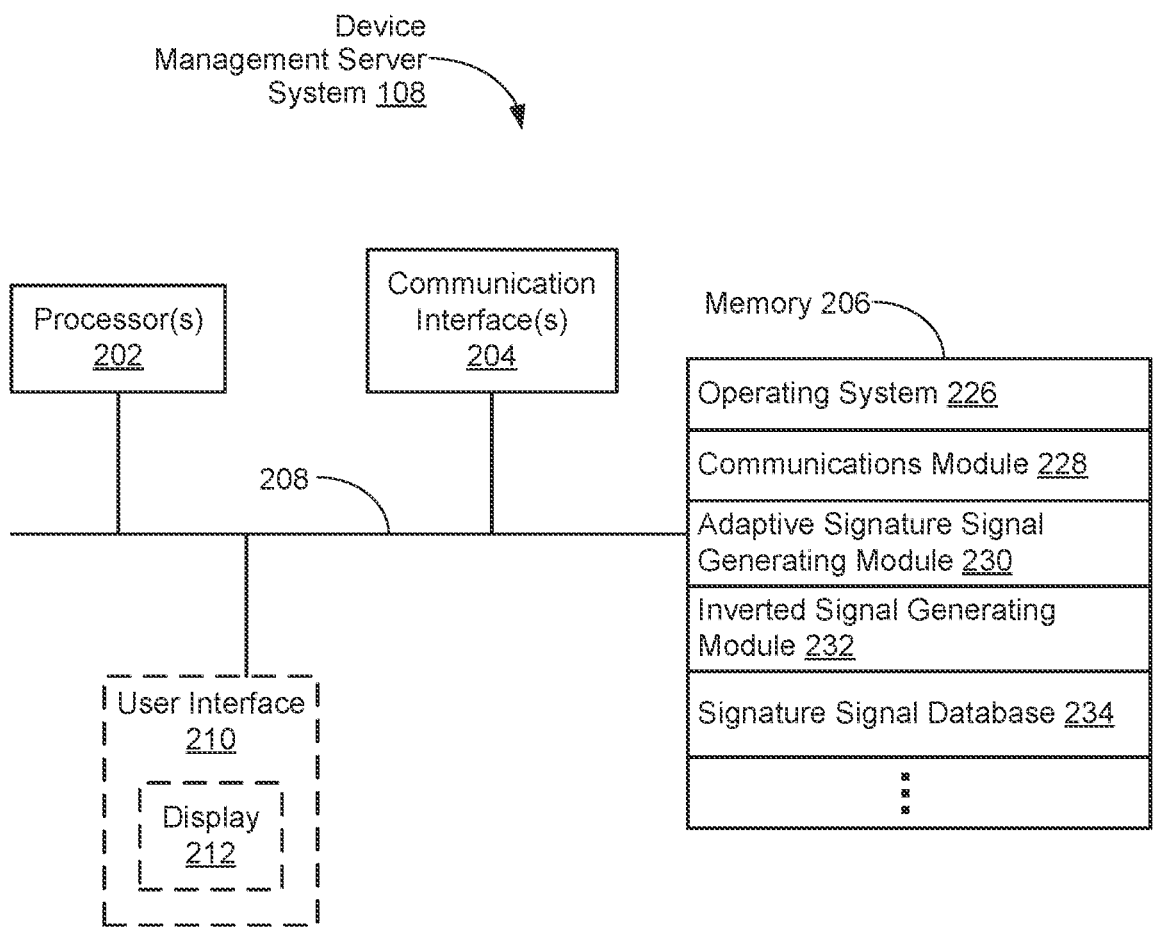
FIG. 2 is a block diagram of an exemplary server system from the architecture of FIG. 1 according to illustrative implementations.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication Turning now to FIG. 2, there is shown a block diagram depicting a device management server 108 in accordance with some implementations. The device management server 108 typically includes one or more processing units (processors or cores) 202, one or more network or other communications interfaces 204 (e.g., one or more antennas), memory 206, and one or more communication buses 208 for interconnecting these components. The communication buses 208 optionally include circuitry (sometimes called a chipset) that interconnects and controls communications between system components. In some implementations, the device management server 108 may include a user interface 210 with a display device 212. In some implementations, the device management server 108 may include input devices such as a keyboard, a mouse, a trackpad, and/or input buttons. In some implementations, the display device 212 may include a touch-sensitive surface, in which case the display is a touch-sensitive display.

The memory 206 may be a high-speed random-access memory, such as DRAM, SRAM, DDR RAM, or other random-access solid-state memory devices, and may include non-volatile memory, such as one or more magnetic disk storage devices, optical disk storage devices, flash memory devices, and/or other non-volatile solid-state storage devices. In some implementations, the memory 206 includes one or more storage devices remotely located from the processor(s) 202. The memory 206, or alternatively the non-volatile memory device(s) within the memory 206, includes a non-transitory computer-readable storage medium. In some implementations, the memory 206 or the computer-readable storage medium of the memory 206 stores programs, modules, and/or data structures that may be used for the performing one or more operations of the server system 108. For example, the memory 206 may include programs, modules, and/or data structures for an operating system 226, a network communication module 228, an adaptive signature signal generating module 230, an inverted signal generating module 232, a signature signal database 234, and/or other modules.

In some implementations, the operating system 226 module may include procedures for handling various basic system services and for performing hardware dependent tasks. The network communication module 228 may be configured for connecting the server system 108 to other computing devices via the one or more communication network interfaces 204 (wired or wireless) and one or more communication networks 106. The adaptive signature signal generating module 230 may be configured to determine a signature signal representative of physical attributes (e.g., sounds and/or vibrations) of a physical environment, the signature signal based on at least sensor data provided by one or more medical devices, user input information, medical device operation information (e.g., power consumption), and/or stored signature signals. A signature signal, in some implementations, is a signal that represents of sounds and/or vibrations proximate to a device. For example, the signature signal can include sound generated by operation of a motor of the medical device and/or surrounding medical devices, and/or vibrations generated by operation of a motor or movement of the medical device and/or surrounding medical devices. A signature signal may include one or more of a magnitude, an amplitude, and a frequency. The inverted signal generating module 232 may be configured to determine an inverted signal based on the determined signature signal and/or a stored signature signal. For example, an inverted signal may be generated with the same frequency as the signature signal but an inverted amplitude. The signature signal database 234 may be configured to store determined signature signals. The stored signature signals can be used instead of determining a new signature signal and/or to determine new signature signals. Alternatively or additionally, in some implementations, the sensor data provided by one or more medical devices, user input information, medical device operation information, and/or other collected data can be stored for future use. Additional details of the grouping and/or categorizing the interactions are described herein with reference to FIG. 4.

Figure 3:
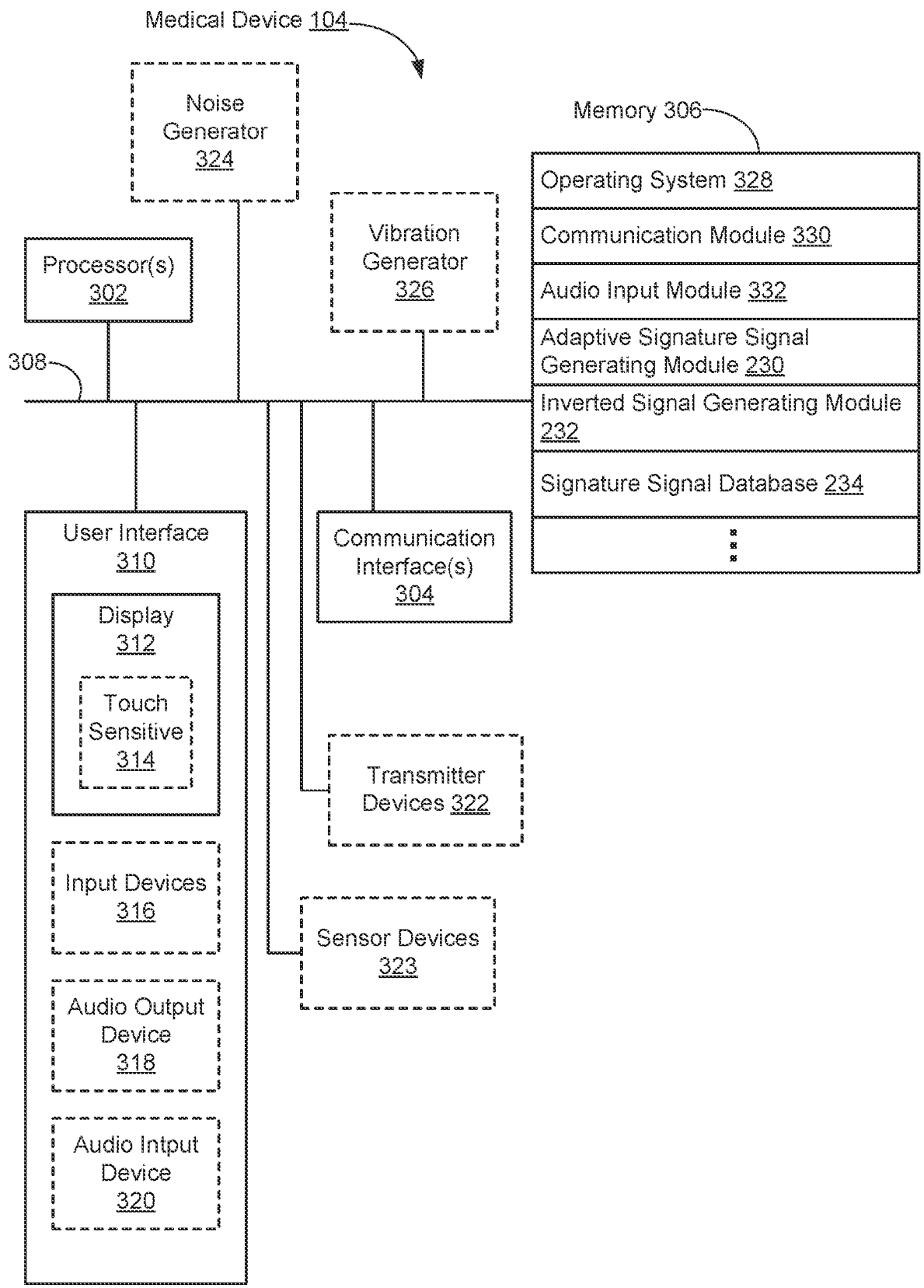
FIG. 3 is a block diagram of an exemplary client device from the architecture of FIG. 1 according to illustrative implementations.

Turning now to FIG. 3, there is shown a block diagram depicting a medical device 104. A medical device 104 may include one or more processors 302, one or more network or communications interfaces 304, memory 306, one or more communication buses 308, a user interface unit 310, transmitter devices 322, and sensor devices 323 (e.g., sound and/or vibration sensors). The one or more processors 302, the one or more network or communication interfaces 304, memory 306, and the user interface unit 310 may be configured to communicate with one another via the one or more communication buses 308. In some implementations, the communication buses 308 may include circuitry (sometimes called a chipset) that interconnects and controls communications between components of the medical device 104. In some implementations, the medical device 104 may include one or more electrical or electromechanical components such as a noise generator 324 (e.g., a speaker) and/or a vibration generator 326 (e.g., a vibration motor).

The user interface unit 310 may include a display 312, one or more input devices 316, such as a keyboard or a mouse, one or more audio output devices 318, and/or one or more audio input devices 320. In some implementations, the display 312 may include a touch sensitive display or surface 314, which is configured to receive inputs from a user 102. The one or more audio output devices 318 may include, but are not limited to, speakers, interfaces configured to transfer audio related data to a device configured to project audio (e.g., audio system within the environment, audio headphones, audio earbuds, hearing aids), and the like. The one or more input devices 320 may include, but are not limited to, microphones, interfaces configured to receive audio related data from a device configured to receive audio.

The memory 306 includes high-speed random-access memory, such as DRAM, SRAM, DDR RAM or other random-access solid-state memory devices; and may include non-volatile memory, such as one or more magnetic disk storage devices, optical disk storage devices, flash memory devices, or other non-volatile solid-state storage devices. In some implementations, the memory 306 includes one or more storage devices remotely located from the processor(s) 302. The memory 306, or alternatively the non-volatile memory device(s) within the memory 306, includes a non-transitory computer-readable storage medium. In some implementations, the memory 306 or the computer-readable storage medium of the memory 306 stores the programs, modules, and data structures that may be used for performing operations of the medical devices 104 and for performing techniques described herein for adaptively cancelling sound and/or vibrations generated by the medical devices 104. The memory 306 may include an operating system 328, a network communication module 330, an audio input/output module 332, an adaptive signature signal generating module 230, an inverted signal generating module 232, a signature signal database 234, and the like. In some implementations, the adaptive signature signal generating module 230, the inverted signal generating module 232, and the signature signal database 234 are the same as those described above in FIG. 2.

The operating system 328 may be configured to perform procedures of execution of various system services of the medical devices 104, including, but not limited to, hardware and software dependent tasks. The network communication module 330 may be configured to execute instructions to connect the medical devices 104 to one or more other computing devices, such as the server system 108, third party servers 110, and the like, via the one or more communication interfaces 304 and communication networks, such as the communication network 106. The audio input module 332 may be configured process received input data and transmit instructions and/or related data to one or more other components of the medical devices 104. In some implementations, the adaptive signature signal generating module 230, the inverted signal generating module 232, and the signature signal database 234 are the same modules as those described above in FIG. 2. For example, the adaptive signature signal generating module 230, the inverted signal generating module 232, and the signature signal database 234 may be implemented in the server 108, both the server 108 and the medical devices 104, in each medical device 104, and/or a subset (less than all) thereof.

The above identified modules and applications may correspond to a set of executable instructions for performing one or more functions as described above and/or in the methods described in this application (e.g., the computer-implemented methods and other information processing methods described herein). One or more of the modules may be implemented as a specific hardware device with the appropriate input and output signal paths. The modules may be combined or otherwise re-arranged in various implementations. In some implementations, the memory 206 and/or the memory 306 store a subset of the modules and data structures identified above. In some implementations, the memory 206 and/or the memory 306 stores additional modules and data structures not described above. Processors 302 may be configured to execute the above identified modules for performing the one or more above-described functions and/or techniques active adaptive noise and vibration control as described herein with reference to FIGS. 4-6.

Figure 4:
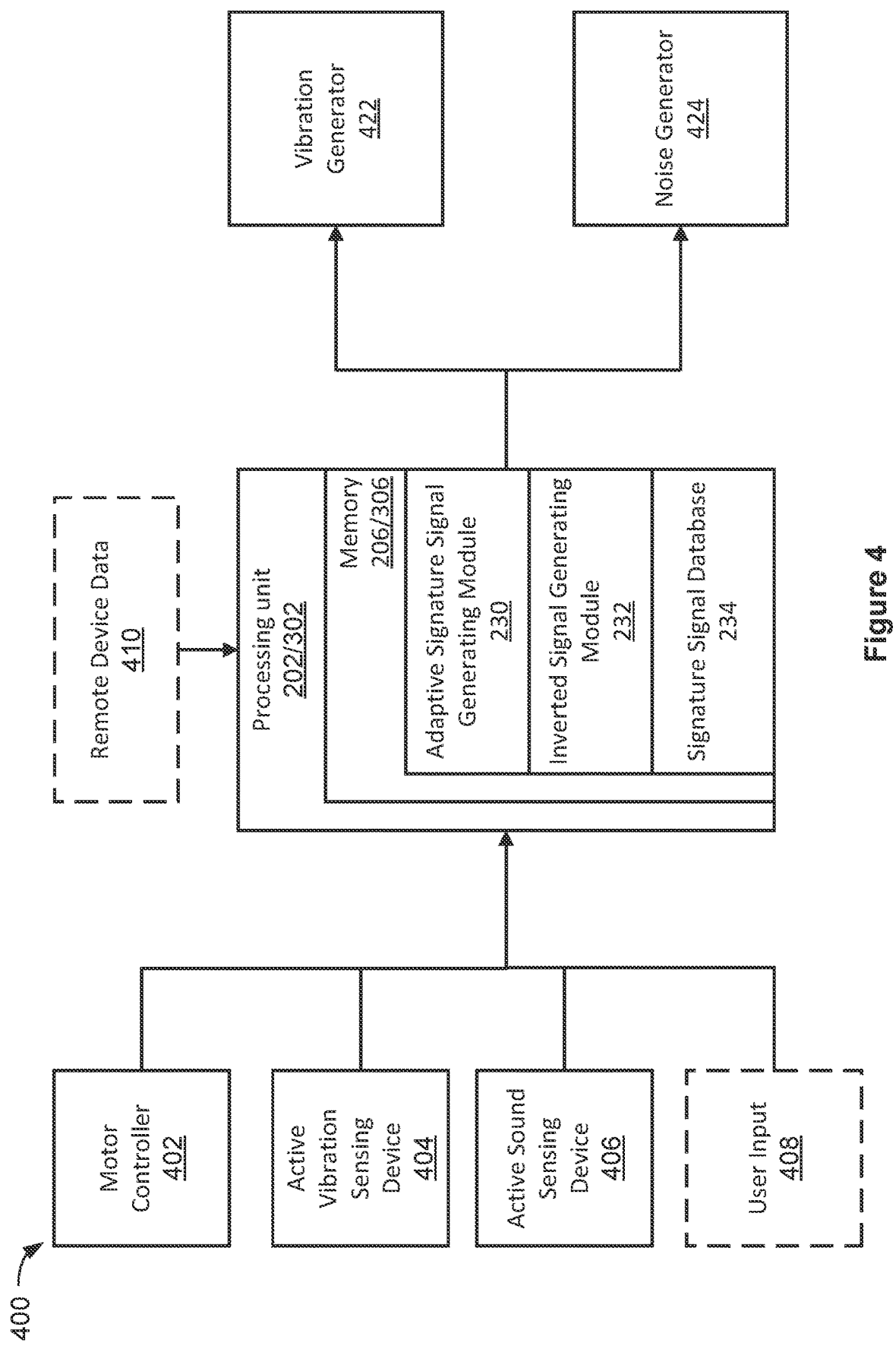
FIG. 4 illustrates an overview of an example active adaptive noise and vibration control according to illustrative implementations.

FIG. 4 illustrates an overview of the active adaptive noise and vibration control 400 according to various implementations of the subject technology. In some implementations, the active adaptive noise and vibration control 400 is part of a medical device 104. In some implementations, the medical device with the active adaptive noise and vibration control 400 is communicatively coupled (e.g., via one or more antennas) or electrically coupled to a server 108, other medical devices 104. Alternatively or additionally, in some implementations, the active adaptive noise and vibration control 400 is part of the server 108 that is electrically coupled or communicatively coupled (e.g., via one or more antennas) to one or more medical devices 104. In some implementations, the active adaptive noise and vibration control 400 is part of a standalone device or a non-transitory computer-readable medium that is configured to electrically and/or communicatively couple to one or more medical devices 104 and/or the server 108.

In some implementations, the active adaptive noise and vibration control 400 is implemented in a single device (e.g., at a medical device 104 and/or at the server 108) that is configured to determine respective signature signals and inverted signals for each communicatively or electrically coupled medical device 104. For example, the active adaptive noise and vibration control 400 can be implemented into the server 108 that is configured to receive data and/or information (as described below) from multiple medical devices 104 and/or other devices (e.g., non-medical devices, such as a smart TV, a laptop, a tablet, etc.), and the server 108 with the active adaptive noise and vibration control 400 will determine respective signature signals and inverted signals for each medical device 104 and/or other device. Alternatively or additionally, in some implementations, the active adaptive noise and vibration control 400 is implemented in a plurality medical devices 104, the server 108, and/or other devices, and each active adaptive noise and vibration control 400 is configured to operate with each other (e.g., in collaboration or concert).

In some implementations, active adaptive noise and vibration control 400 is electrically and/or communicatively coupled to a motor controller 402 configured to control one or more motors and/or pumps of the medical device 104. In some implementations, the motor controller 402 is configured to obtain operation information for one or more motors and/or pumps of the medical device 104. In some implementations, the operational information includes power consumption information for each motor and/or pump of the medical device 104. Power consumption information, in some implementations, includes at least a voltage, frequency, and/or current usage of each motor and/or pump controlled by the motor controller 402. In some implementations, the motor controllers 402 provides the operational information to a processing unit 202/302 to determine a signature signal as described below.

In some implementations, active adaptive noise and vibration control 400 is electrically and/or communicatively coupled to an active vibration sensing device 404. In some implementations, the active vibration sensing device 404 includes at least one of an accelerometer, displacement sensor, velocity sensor, and/or other similar sensors for determining vibrations. In some implementations, the active vibration sensing device 404 obtains data for vibrations generated by operation of a medical device 104 (e.g., one or more physical byproducts of the medical device). In some implementations, the vibrations generated by operation of a medical device 104 include operation of the pumps and/or motors, movement of fluid within the medical device, operation of cooling fans, and/or other functions of the medical device. In some implementations, the active vibration sensing device 404 obtains vibration data based on one or more environmental conditions of a physical environment proximate to the medical device. Proximate, in some implementations, means within 3 feet, 10 feet, 20 feet, 30 feet, or in the same room. In some implementations, vibration data based on one or more environmental conditions of a physical environment proximate to the medical device 104 include vibrations generated by surrounding medical devices and/or other devices (e.g. MRI machines, heart rate monitors, fans, HVAC systems, ambient traffic, elevators, computing devices, etc.), vibrations detected based on movement (e.g., movement of the medical devices 104 or other devices caused by its operation and/or movement of the medical device 104 by a medical practitioner or patient), vibrations detected by a user interaction with the medical devices 104 or other device (e.g., medical practitioners configuring the medical device 104), vibrations detected by a user movement (e.g., motion of the patients using the medical device), and/or other sources of vibration. The examples provided above are non-exhaustive and any vibrations captured by the active vibration sensing device 404 can be used to determine a signature signal. In some implementations, the active vibration sensing device 404 provides the data to the processing unit 202/302 to determine a signature signal as described below.

In some implementations, active adaptive noise and vibration control 400 is electrically and/or communicatively coupled to an active sound sensing device 406. In some implementations, the active sound sensing device 406 includes at least one of a sound transducer, a microphone, and/or other audio input devices or sensors for detecting sound. In some implementations, the active sound sensing device 406 obtains data for sounds generated by operation of the medical device 104 (e.g., one or more physical byproducts of the medical device 104). In some implementations, the sounds generated by operation of a medical device include operation of an infusion pump (e.g., a peristaltic pump), one or more related motors, movement of fluid within the medical device or fluid delivery set (e.g., tubing, valves, catheter, etc.) associate with the medical device, operation of cooling fans, and/or other functions of the medical device. In some implementations, the active sound sensing device 406 obtains sound data based on one or more environmental conditions of a physical environment proximate to the medical device 104. In some implementations, sound data based on one or more environmental conditions of a physical environment proximate to the medical device 104 include sound generated by surrounding medical devices and/or other devices, sound detected based on movement of the medical devices 104 or other devices, sound reflected by one or more walls (e.g., by the medical device or other medical devices), sound detected by a user interaction with the medical devices 104 or other device, sound detected by a user movement, and/or other sources of sound (see the additional examples provided above). The examples provided above are non-exhaustive and any audio captured by the active sound sensing device 406 can be used to determine a signature signal. In some implementations, the active sound sensing device 406 provides the data to the processing unit 202/302 to determine a signature signal as described below.

In some implementations, active adaptive noise and vibration control 400 is configured to receive user input 408. In some implementations, the user input 408 is received via a user interface coupled to the medical devices 104, the server 108, and/or other devices. For example, the via user interface can be a touch screen display, a desktop computer, laptop computer, voice inputs, gesture inputs and/or variations thereof. Alternatively or additionally, in some implementations, the user input 408 is received via a remote device such as without limitation, a mobile phone, a PDA, and/or a tablet. In some implementations, the user input 408 is received via mobile applications, Web browsers, and/or other variations thereof. In some implementations, the user input 408 includes information about the physical environment proximate to a medical device 104 (or the server 108, other medical devices, and/or other devices).

A non-exhaustive list of the user input information includes at least one of a number of other active medical devices and/or inactive medical devices proximate to the medical device 104, a location of the medical device 104, other non-medical devices proximate to the medical device 104, a number of patients proximate to the medical device 104, and/or a configuration of the medical device 104; other medical device; and/or non-medical devices. For example, the user input 408 can provide information indicating that the medical device 104 is located in an intensive care unit (ICU) that includes multiple medical devices, at a location with ambient traffic (e.g., visitors and medical personnel walking around), at a location adjacent to elevators, and/or at a location that may be larger than a private room. In another example, the user input 408 can provide information that the medical device 104 is proximate to an MRI machine or other device that is known to generate loud sounds and strong vibrations. A brief listing of examples for the configuration of the medical device 104 include the selected power level, the number of motors and/or pumps that are active (e.g., being used), one or more components and/or modules attached to the medical device 104 (e.g., additional motors and/or pumps coupled to the medical device 104), the strength at which the motors and/or pumps are operating (e.g., at what flow rate a fluid is being moved via the medical device 104). User input 408 can include any information relevant for determining the sources of vibration and generation proximate to a medical device and/or other devices (e.g., the server 108 and/or non-medical devices) that implement the active adaptive noise and vibration control 400. In some implementations, the active adaptive noise and vibration control 400 provides the user input 408 to the processing unit 202/302 to determine a signature signal as described below.

In some implementations, the active adaptive noise and vibration control 400 is communicatively coupled via one or more antennas. The active adaptive noise and vibration control 400 is configured to receive data and/or information (referred to as remote device data 410) from respective medical devices 104, the server 108, and/or other devices that are electrically and/or communicatively coupled to the active adaptive noise and vibration control 400. In some implementations, the remote device data 410 includes, from each electrically and/or communicatively coupled device, data and/or information from a motor controller 402, active vibration sensing device 404, active sound sensing device 406, user input 408, and/or any other sensors. The remote device data 410 is provided to the processing unit 202/302 to determine a signature signal as described below. Similarly, in some implementations, the active adaptive noise and vibration control 400 is configured to provide its respective data and/or information from the motor controller 402, active vibration sensing device 404, active sound sensing device 406, user input 408, and/or any other sensors to other medical devices, the server 108, and/or other devices.

In some implementations, the processing unit 202/302 is coupled to a memory 206/306, the memory including at least an adaptive signature signal generating module 230, an inverted signal generating module 232, and a signature signal database 234. In some implementations, the processing unit 202/302 uses the adaptive signature signal generating module 230 to determine a signature signal based on at least one of the data and/or information provided by the motor controller 402, the active vibration sensing device 404, and/or the active sound sensing device 406. In some implementations, the signature signal is a representation of physical attributes of a physical environment proximate to the medical device including one or more physical byproducts of the medical device 104, and one or more environmental conditions of a physical environment proximate to the medical device 104 (e.g., sounds and/or vibrations generated by the medical device 104 or the surrounding environment of the medical device 104).

In some implementations, the adaptive signature signal generating module 230 uses the power consumption information (included in the operational information provided by the motor controller 402) to determine (all or part of) a signature signal for the sound and/or vibration generated each motor and/or pump controlled by the motor controller 402. In some implementations, the adaptive signature signal generating module 230 can determine (e.g., predict) an expected vibration and/or sounds generated by the one or more motors and/or pumps of the medical device 104 based on the power consumption information. In some other implementations, the type of motors and/or pumps used by the medical device 104 are known, and the power consumption information is used by the adaptive signature signal generating module 230 to accurately determine an expected vibration and/or sounds generated by the one or more motors and/or pumps of the medical device 104. The adaptive signature signal generating module 230 uses the determined vibration and/or sounds generated by the one or more motors and/or pumps of the medical device 104 to determine the signature signal (representative of the determined or captured sounds and/or vibrations).

In some implementations, the adaptive signature signal generating module 230 uses the data provided by the active vibration sensing device 404 and/or the active sound sensing device 406 to determine (all or part of) the signature signal for the sound and/or vibration generated the medical device 104, other medical devices, surrounding devices, and/or environmental conditions (a non-exhaustive list of examples provided above). For example, the active vibration sensing device 404 can determine a vibration and/or sounds caused by one or more motors and/or pumps of a medical device 104, caused by movement of the medical device 104, caused by a patient attached to the medical device 104, caused by surrounding devices (medical or non-medical; such as an MRI machine, heart rate monitors, HVAC systems, ambient traffic, elevators, computing devices, and/or an air conditioner/fan), and/or any other source that may generate vibrations and/or sounds. The adaptive signature signal generating module 230 determines a signature signal representative of all of the (sound and/or vibration) data provided by the active vibration sensing device 404 and/or the active sound sensing device 406 (representative of the determined sounds and/or vibrations).

In some implementations, the adaptive signature signal generating module 230 uses the user input 408 information to determine (all or part of) the signature signal for the sound and/or vibration generated the medical device 104, other medical devices, surrounding devices, and/or environmental conditions (a non-exhaustive list of examples provided above). In some implementations, the adaptive signature signal generating module 230 can use the user input 408 information represent vibrations and/or sounds that would not be captured by the motor controller 402, the active vibration sensing device 404, and/or the active sound sensing device 406. In particular, the adaptive signature signal generating module 230 can use the user input 408 information to account for the environmental conditions and/or configuration of the devices (medical or non-medical). For example, user input 408 information indicating that the medical device 104 is in a small or private room can be used to the adaptive signature signal generating module 230 to account for reflected sounds against the wall, sounds of higher magnitude, higher occurrence of movement because of the smaller space, and/or a number of factors as described above. Similarly, the user input 408 information can help the adaptive signature signal generating module 230 identify the location of the medical device 104 (e.g., a particular care area including its layout, other medical devices in the care area, etc.). The adaptive signature signal generating module 230 can determine a signature signal representative of physical attributes (e.g., sounds and/or vibrations) described in and/or expected from the user input 408 information (e.g., MRI machine (or other medical devices) located in the same room as the medical device 104, room size, ambient traffic, and/or other user input described herein). Alternatively or additionally, in some implementations, the adaptive signature signal generating module 230 can use the user input 408 information to augment the data provided by the active vibration sensing device 404 and/or the active sound sensing device 406.

In some implementations, the remote device data 410 is used by the adaptive signature signal generating module 230 in conjunction with the data and/or information provided by the motor controller 402, the active vibration sensing device 404, the active sound sensing device 406, and/or user input 408. In some implementations, the adaptive signature signal generating module 230 uses the remote device data 410 to improve the accuracy of a determined signature signal. For example, the remote device data 410 can be used to verify and/or improve (or refine) the data and/or information provided by the motor controller 402, the active vibration sensing device 404, the active sound sensing device 406, and/or user input 408. Alternatively or additionally, in some implementations, the adaptive signature signal generating module 230 can use the remote device data 410 to improve the overall signature signal by accounting for sounds or vibrations that were not provided by the data and/or information provided by the motor controller 402, the active vibration sensing device 404, the active sound sensing device 406, and/or user input 408. For example, a single device may not be able to capture all of the generated vibrations and/or sounds in its proximate environment; however, other devices (medical and/or non-medical) in the same proximate environment as the single device and/or a server 108 communicatively or electrically coupled to the single device are able to capture the generated vibrations and/or sounds that the single device was not able to capture. Using the remote device data 410, the adaptive signature signal generating module 230 can determine a complete signature signal representative of sounds and/or vibrations proximate to the single device.

The adaptive signature signal generating module 230 can use all of the data and/or information described above in individually and/or in any combination. For example, the adaptive signature signal generating module 230 can use all of the data and/or information to generate a signature signal based on all of the available information. In another example, the adaptive signature signal generating module 230 can use the data from a single source (e.g., the active vibration sensing device 404) to generate a signature signal. In yet another example, the adaptive signature signal generating module 230 can use the data and/or information from a subset (less than all) of source (e.g., user input 408 information and the active sound sensing device 406) to generate a signature signal.

In some implementations, the processing unit 202/302 uses the inverse signal generating module 232 to determine an inverse signal based on the signature signal determined by the adaptive signature signal generating module 230. In some implementations, the inverse signal generating module 232 determines an inverse that is configured to cancel (e.g., nullify or deconstructively interfere with) the determined signature signal. The determined inverse signal, when generated by the one or more electrical or electromechanical components (as discussed below), causes the generation of a physical representation of the inverse signal that cancels the physical attributes of the environment represented by the signature signal. In this way, the inverse signal, by being generated, is configured to reduces or eliminates the noise and/or vibrations generated by the medical device 104. In particular, the determined inverse signal is configured to reduce or eliminate the noises and/or vibrations represented in the determined signature signal. By utilizing the inverse signal, patients are not bothered by the constant sounds and vibrations that are present in medical rooms.

In some implementations, the signature signal generated by the adaptive signature signal generating module 230 is stored in the signature signal database 234. In some implementations, the stored signature signals in the signature signal database 234 can be used, by the inverse signal generating module 232, to determine an inverse signal. In some implementations, using stored signature signals 234 reduces the time to generate an inverse signal by having an initial baseline signature signal. For example, in some implementations, a medical device remains in one patient care room or is moved into a new care room. A stored signature signal for the patient rooms can be used as the signature signal or can be used to determine a new signature signal, if necessary (e.g., necessary if there are changes that need to be accounted for). In some implementations, the stored signature signal can be used with the data and/or information provided by the motor controller 402, the active vibration sensing device 404, the active sound sensing device 406, user input 408, and/or remote device data 410 to determine a new signature signal (by the adaptive signature signal generating module 230). In this way, stored signature signal can be used to improve the performance of the active adaptive noise and vibration control 400 by allowing the active adaptive noise and vibration control 400 to learn and build on previously determined signature signals.

In some implementations, the active adaptive noise and vibration control 400 provides the determined inverse signal to one or more electrical or electromechanical components of the medical device 104. In some implementations, the one or more electrical or electromechanical components of the medical device 104 include a vibration generator 422 and/or noise generator 424. In some implementations, the vibration generator 422 includes oscillators, coil springs, vibration motors (e.g., haptic motors, linear resonant actuator, brushless vibration motors, etc.), and/or other types of vibration generators. In some implementations, noise generator 424 includes electrical noise generators, sound generators (e.g. white-noise machines), speakers, loudspeakers, and/or similar devices. In some implementations, the vibration generator 422 and/or the noise generator 424 produce (or generate) physical representation of the inverse signal. The physical representation of the inverted signal is configured to cancels the physical attributes of the environment represented by the signature signal. In particular, the vibration generator 422 and/or noise generator 424 use the inverse signal to generate vibrations and sounds to cancel or deconstructively interfere with the sounds and/or vibrations in an environment of the medical device 104. As such, the more accurate that the physical environment is represented by the signature signal, the more efficiently and effectively that the determined inverse signal can be used to cancel the physical attributes (e.g., by generation of a physical representation of the inverse signal.

Figure 5:
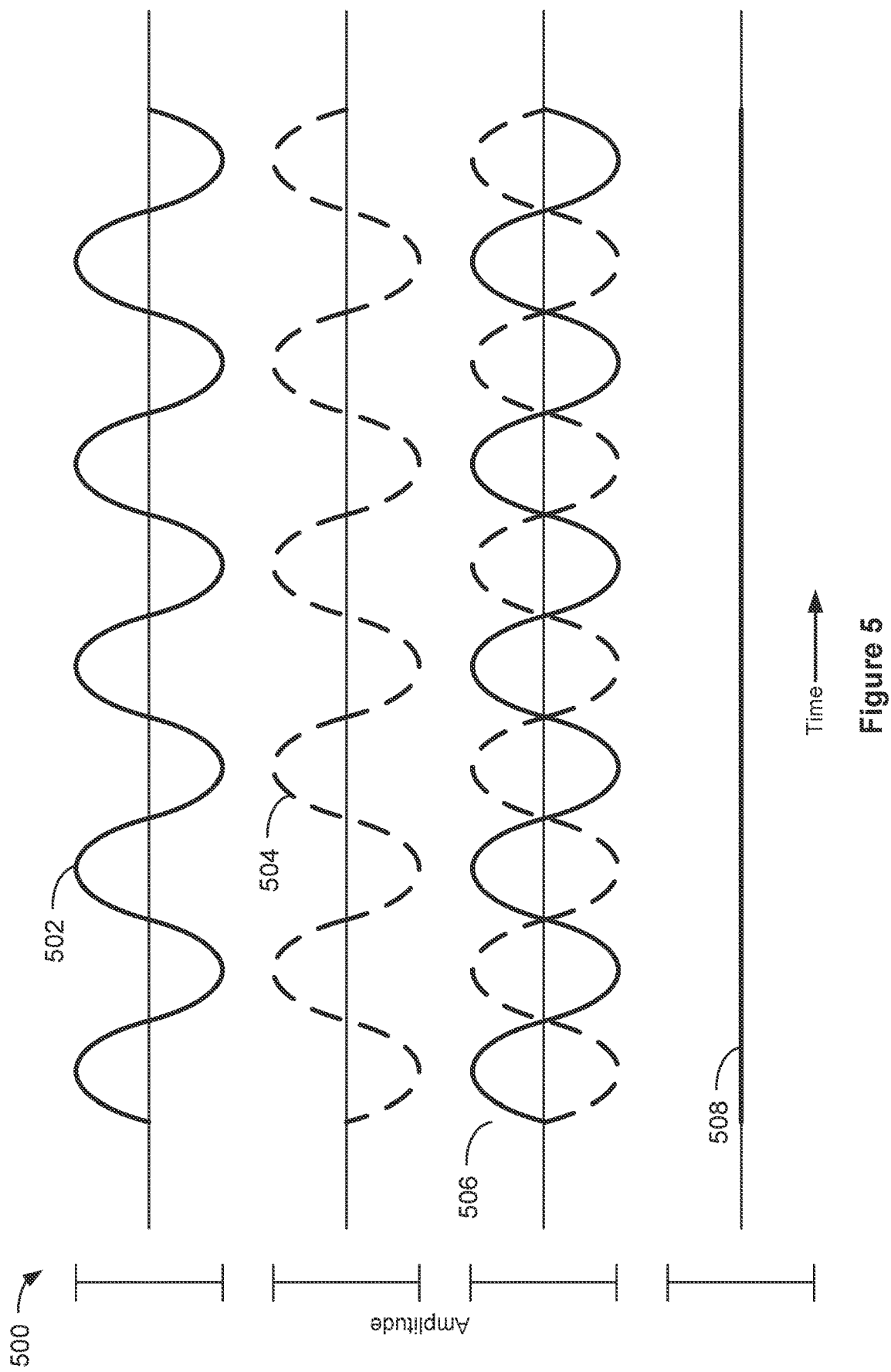
FIG. 5 illustrates example adaptive signal cancellation plots for the active adaptive noise and vibration control according to illustrative implementations.

FIG. 5 illustrates adaptive signal cancellation plots 500 for the active adaptive noise and vibration control according to various implementations of the subject technology. The adaptive signal cancellation plots 500 are in the time domain and show the signals across time (x-axis) and their respective amplitudes (y-axis).

FIG. 5 shows a signature signal 502. In some implementations, the signature signal 502 is determined based on data and/or information received from at least one of the motor controller 402, the active vibration sensing device 404, the active sound sensing device 406, user input 408, remote device data 410, and/or stored signature signal. Determination of the signature signal 502 is described above in FIG. 4. FIG. 5 also shows an inverse signal 504. In some implementations, the inverse signal 504 is determined based on the signature signal 502 (e.g., either a determined signature signal or a stored signature signal). Determination of the inverse signal 504 is described above in FIG. 4. As further shown in FIG. 5, superimposed signal 506 includes the signature signal 502 and the inverse signal 504 (superimposed). The signal 502 and the inverse signal 504 are exact or near exact opposites of one another. In this way, both the signal 502 and the inverse signal 504 will cancel each other out and/or nullify each other. For example, as shown in cancelled signal 508, both the signal 502 and the inverse signal 504 have cancelled each other out such that they are not detected.

Figure 6B:
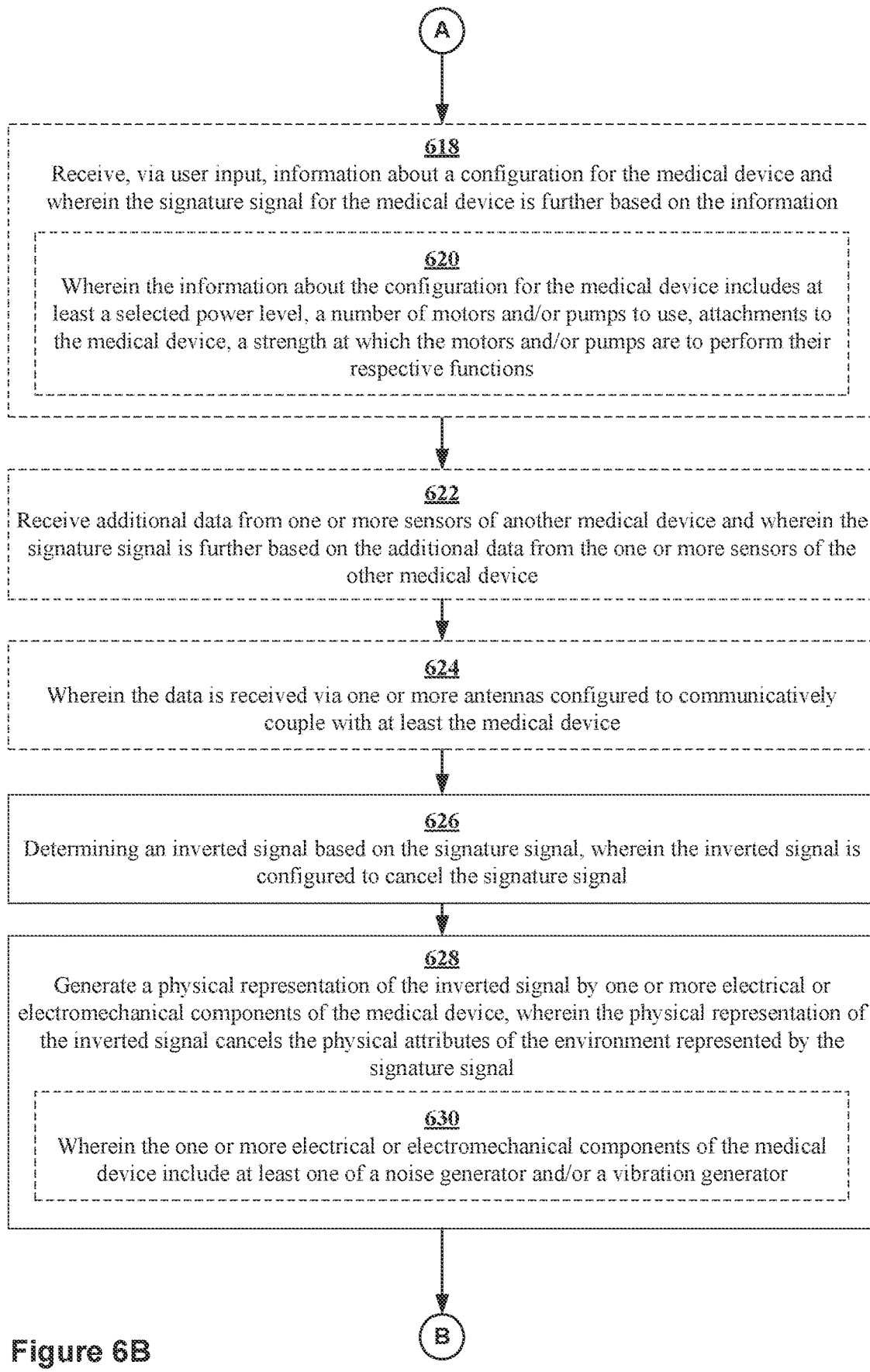

FIGS. 6A-6C are flowcharts illustrating a method 600 for active adaptive noise and vibration control according to some implementations. Method 600 may be performed at one or more medical devices 104 and/or the server 108. At least some of the operations in method 600 may be performed by a computer having a processor executing commands stored in a memory of the computer (e.g., processors 202 and 302, and memories 206 and 306). In some implementations, operations as disclosed in method 600 may include retrieving, editing, and/or storing files in a database that is part of, or is communicably coupled to, a memory (e.g., memories 206 and 306). In some implementations, information transmitted between one or more devices in a system performing method 600 may include sensor data and/or user input information (as described below). Methods consistent with the present disclosure may include at least some, but not all, of the operations illustrated in method 600, performed in a different sequence. Furthermore, methods consistent with the present disclosure may include at least two or more steps as in method 600 performed overlapping in time, or almost simultaneously.

Method 600 includes receiving (602) data from one or more sensors of a medical device 104. In some implementations, the one or more sensors of the medical device 104 include (604) at least one of an accelerometer, displacement sensor, velocity sensor, sound sensors, sound transducers. In some implementations, the one or more sensors are used to capture vibration and/or sound signals. For example, in some implementations, a sound sensor can include a microphone and/or similar devices configured to capture sound.

Method 600 includes determining (606) a signature signal for the medical device 104 based at least on the data. The signature signal is a representation of physical attributes of a physical environment proximate to the medical device including one or more physical byproducts of the medical device 104, and one or more environmental conditions of the physical environment proximate to the medical device 104. Proximate, in some implementations, means within 3 feet, 10 feet, 20 feet, 30 feet, or in the same room. For example, the one or more physical byproducts of the medical device 104 can include sound and/or vibrations generated by operating motors, fans, and/or pumps of the medical device 104; movement of the medical device 104; movement of fluids and/or other substances within the medical device 104; and/or any other sources of generated energy within the medical device 104 that cause sound and/or vibrations to be heard and/or felt. Examples of one or more environmental conditions of the physical environment proximate to the medical device 104 can include sounds and/or vibrations generated by other similar or different medical devices (e.g., MRI machines, x-ray machines, monitors, infusion pumps, and/or other medical devices) within the same room of as the medical device 104, echoes and/or reflected sounds (e.g., sounds bouncing off one or more walls in a room), sounds and/or vibrations generated by other devices (e.g., fans, HVAC systems, computing devices, lights, television, radio, etc.) within the same room of as the medical device 104, and/or other ambient sounds or vibrations within a room (e.g., generated by ambient traffic (e.g., visitors, medical staff, and/or other patients within or around the room), elevators, etc.). In some implementations, the signature signal includes (608) at least one of a sound signal and/or vibration signal.

In some implementations, the method includes receiving (610) operation information from at least one or more motor controllers of the medical device 104, and the signature signal for the medical device 104 is further based on the operational information. In some implementations, the operational information includes (612) at least a voltage, frequency and/or current usage of one or more motors as controlled by the one or more motor controllers. In other words, the operation information includes power consumption of one or more motors and/or pumps of the medical device 104. Power consumption, in some implementations, means the current used by the one or more motors and/or pumps, voltage provided the one or more motors and/or pumps, frequency of the motors and/or pumps of the medical device 104. For example, in some implementations, the method determines the vibration and/or sounds generated by the one or more motors and/or pumps of the medical device 104 based on the power consumption of one or more motors and/or pumps of the medical device 104. In some implementations, because the type of motors and/or pumps within a medical device 104 are known, the power consumption information enables the system to accurately determine an expected vibration and/or sounds generated by the one or more motors and/or pumps of the medical device 104.

In some implementations, the method 600 includes receiving (614), via user input, information about the physical environment proximate to the medical device 104, and the signature signal for the medical device 104 is further based on the information. In some implementations, the information about the physical environment proximate to the medical device 104 includes (616) at least one of a number of other active medical devices and/or inactive medical devices proximate to the medical device 104, a location of the medical device 104, and/or a configuration of the medical device 104. For example, a user may indicate a particular room in which the medical device 104 is located (e.g., first care area, second care area, etc.) and the room may include one or more devices (e.g., MRI machines, monitors, fans, HVAC systems, elevators, computing devices, and/or other sound and/or vibration generating devices). The information provided by the user allows the method to compensate for the additional medical devices. For example, if it is known that a particular room contains an MRI machine, a signature signal for the MRI machine can be determined.

Alternatively or additionally, in some implementations, the method 600 includes receiving (618), via user input, information about a configuration for the medical device 104 or other devices (e.g., other medical devices and/or non-medical devices), and the signature signal for the medical device 104 is further based on the information. In some implementations, the information about the configuration for the medical device 104 includes (620) at least one of a selected power level, a number of motors and/or pumps to use, attachments to the medical device 104, a strength at which the motors and/or pumps are to perform their respective functions. For example, a user can specify that the medical device 104 is to operate at a particular power level (e.g., high, moderate, low power levels), a particular number of motors and/or pumps are to be used, a strength at which the motors and/or pumps are to perform their respective functions, and/or other configurations specific to the medical device 104. In another example, the medical device 104 may be configured to attach to one or more components such as additional motors, additional sensors, communication components, etc., and the information about a configuration for the medical device 104 may include a type of attachment, the number of attachments, settings of the attachment, and similar information.

In some implementations, the method 600 includes receiving (622) additional data from one or more sensors of another medical device, and the signature signal is further based on the additional data from the one or more sensors of the other medical device. In some implementations, the other medical device provide respective information as indicated above. For example, the medical devices 104 can receive, from the other medical device respective operation information from at least one or more motor controllers of the other medical device, respective information about the physical environment proximate to the other medical device, respective information about a configuration for the other medical device. Any variation of information received from one or more other medical devices can be used by the medical device to determine the signature signal. As another example, the additional sensor signal may indicate time, movement, power state, or pump configuration (e.g., number of modules attached to the PCU). The signal may be generated by a clock, accelerometer, voltage monitor, or pump configuration monitor. Additional sensor information may be used as a factor to determine a characteristic of the signal to emit (e.g., wavelength, volume, frequency, etc.). Additional sensor information may additionally or alternatively be used to determine whether to emit the signature signal. In such instances, the time of day, amount of movement, on/off/sleep state, or number of modules may be used to dynamically generate a threshold for signal emission or select a process for generating an inversion signal. For example, during the night, when a patient may be asleep, it may be desirable to generate an inversion signal having a lower strength than during the day to reduce the likelihood of waking the sleeping patient.

In some implementations, the data is received (624) via one or more antennas configured to communicatively couple with at least the medical device. Similarly, in some implementations, the additional received information (described in operations 610-622) can also be received via the one or more antennas.

The method 600 includes determining (626) an inverted signal based on the signature signal, wherein the inverted signal is configured to cancel the signature signal. The method 600 includes generating (628) a physical representation of the inverted signal by one or more electrical or electromechanical components of the medical device 104, wherein the physical representation of the inverted signal cancels the physical attributes of the environment represented by the signature signal. In some implementations, the one or more electrical or electromechanical components of the medical device 104 include (630) at least one of a noise generator (e.g., a speaker and/or other sound generating machine), vibration generator (e.g., oscillators, coil springs, vibration motors, and/or other similar devices).

In some implementations, the method 600 includes determining (632-a) respective signature signals for the medical device 104 and the other medical device based at least on the data and the additional data. In some implementations, the method 600 includes determining (632-b) respective inverted signals based on the respective signature signals, wherein the respective inverted signals are configured to cancel the respective signature signals. In some implementations, the method 600 includes generating (632-c) respective physical representations of the respective inverted signals by one or more respective electrical or electromechanical components of the medical device and the other medical device, wherein the respective physical representations of the respective inverted signals cancel respective physical attributes of the environment represented by the respective signature signals. In this way, the method 600 is able to adaptively cancel the physical attributes of an environment represented by signature signal of multiple medical devices. In particular, the method 600 uses all of the received data (from the medical device 104 and other medical devices) to determine an accurate representation of the physical attributes of the environment (via signature signals) for each device, and to determine a respective inverted signal to cancel out each signature signal for each device, and ultimately the physical attributes of the environment when the physical representations of the inverted signals are generated.

In some implementations, after cancelling the physical attributes of the environment represented by the signature signal, the method 600 includes storing (634) at least the signature signal. In some implementations, the method includes storing one or more of the received data from one or more sensors, operation information from at least one or more motor controllers, information (environmental or medical device based) from user input, and/or additional data from one or more sensors of other medical devices. In some implementations, the method 600 includes receiving (636-*a*) subsequent data from the one or more sensors of the medical device 104. The method 600 includes determining (636-*b*) a subsequent signature signal for the medical device 104 based on the subsequent data and the stored signature signal. The method 600 includes determining (636-*c*) a subsequent inverted signal based on the subsequent signature signal, wherein the subsequent inverted signal is configured to cancel the subsequent signature signal. The method 600 includes generating (636-*d*) a physical representation of the subsequent inverted signal by the one or more electrical or electromechanical components of the medical device 104, wherein the physical representation of the subsequent inverted signal cancels the physical attributes of the environment represented by the subsequent signature signal. In this way, the method 600 is able to adaptively learn by continuously storing data and/or determined signature signals for future use. Further, this allows the method 600 adaptively cancel signals (and physical representations thereof) faster by using previously determined signature signals.

In some implementations, information about the inversion signal may be provided to the medical device 104 and used by the medical device 104 to control one or more element included therein. For example, an infusion device may include one or more sensor to detect a characteristic of the fluid. The detection may be based on vibrations measured by the one or more sensors. In implementations where an inversion signal is being deliberately generated, it may be desirable to provide this information to the infusion device to disambiguate vibrations that are truly a characteristic of the fluid from vibrations that are generated externally (e.g., by an inverting signal generator).

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (e.g., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other implementations.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, C, C++, web services, or rich site summary (RSS). In some embodiments, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and implementations of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A system, comprising:
a memory storing instructions; and
one or more processors coupled with the memory and configured to execute the instructions to cause the system to:
receive, via user input, information about a physical environment proximate to the medical device;
receive data from one or more sensors of a medical device;
determine a signature signal for the medical device based at least on the information and the data, wherein the signature signal is a representation of physical attributes of the physical environment proximate to the medical device including:
one or more physical byproducts of the medical device, and
one or more environmental conditions of the physical environment proximate to the medical device;
determine an inverted signal based on the signature signal, wherein the inverted signal is configured to cancel the signature signal; and
generate a physical representation of the inverted signal by one or more electrical or electromechanical components of the medical device,
wherein the physical representation of the inverted signal cancels the physical attributes of the environment represented by the signature signal.

2. The system of claim 1, further comprising instructions that, when executed by the one or more processors, cause the system to:
receive operation information from at least one or more motor controllers of the medical device; and
wherein the signature signal for the medical device is further based on the operational information.

3. The system of claim 2, wherein the operational information includes at a frequency and/or current usage of one or more motors controlled by the one or more motor controllers.

4. The system of claim 1, wherein the information about the physical environment proximate to the medical device includes at least one of a number of other active medical devices and/or inactive medical devices proximate to the medical device, a location of the medical device, other non-medical devices proximate to the medical device, a number of patients proximate to the medical device, and/or a configuration of the medical device or other devices.

5. The system of claim 1, further comprising instructions that, when executed by the one or more processors, cause the system to:
receive, via user input, information about a configuration for the medical device; and
wherein the signature signal is further based on the information.

6. The system of claim 5, wherein the information about the configuration for the medical device includes at least one of a selected power level, a number of motors and/or pumps to use, a strength at which the motors and/or pumps are to perform their respective functions.

7. The system of claim 1, further comprising instructions that, when executed by the one or more processors, cause the system to:
receive additional data from one or more sensors of another medical device; and
wherein the signature signal is further based on the additional data from the one or more sensors of the other medical device.

8. The system of claim 7, further comprising instructions that, when executed by the one or more processors, cause the system to:
determine respective signature signals for the medical device and the other medical device based at least on the data and the additional data;
determine respective inverted signals based on the respective signature signals, wherein the respective inverted signals are configured to cancel the respective signature signals;
generate respective physical representations of respective inverted signals by one or more respective electrical or electromechanical components of the medical device and the other medical device,
wherein the respective physical representations of the respective inverted signals cancel respective physical attributes of the environment represented by the respective signature signals.

9. The system of claim 1, further comprising instructions that, when executed by the one or more processors, cause the system to:
after cancelling the physical attributes of the environment represented by the signature signal, store at least the signature signal.

10. The system of claim 9, further comprising instructions that, when executed by the one or more processors, cause the system to:
receive subsequent data from the one or more sensors of the medical device;
determine a subsequent signature signal for the medical device based on the subsequent data and a stored signature signal;
determine a subsequent inverted signal based on the subsequent signature signal, wherein the subsequent inverted signal is configured to cancel the subsequent signature signal;
generate a physical representation of the subsequent inverted signal by the one or more electrical or electromechanical components of the medical device,
wherein the physical representation of the subsequent inverted signal cancels the physical attributes of the environment represented by the subsequent signature signal.

11. The system of claim 1, wherein the signature signal includes at least one of an audio signal and/or vibration signal.

12. The system of claim 1, wherein the one or more sensors of the medical device include at least one of an accelerometer, displacement sensor, velocity sensor, sound sensors, sound transducers.

13. The system of claim 1, wherein the one or more electrical or electromechanical components of the medical device include at least one of a noise generator and/or a vibration generator.

14. The system of claim 1, further comprising one or more antennas configured to communicatively couple with at least the medical device.

15. A computer-implemented method, comprising:
receive, via user input, information about the physical environment proximate to the medical device;
receiving data from one or more sensors of a medical device;
determining a signature signal for the medical device based at least on the information and the data, wherein the signature signal is a representation of physical attributes of the physical environment proximate to the medical device including:
one or more physical byproducts of the medical device, and
one or more environmental conditions of the physical environment proximate to the medical device;
determining an inverted signal based on the signature signal, wherein the inverted signal is configured to cancel the signature signal; and
generating a physical representation of the inverted signal by one or more electrical or electromechanical components of the medical device,
wherein the physical representation of the inverted signal cancels the physical attributes of the environment represented by the signature signal.

16. The method of claim 15, further comprising:
receiving operation information from at least one or more motor controllers of the medical device; and
determining the signature signal for the medical device based on at least the data and the operational information.

17. The method of claim 15, further comprising:
receiving additional data from one or more sensors of another medical device; and
determining the signature signal for the medical device based on at least the data and the additional data from the one or more sensors of the other medical device.

18. A non-transitory, computer-readable medium storing instructions which, when executed by a processor in a computer, cause the computer to perform a method, the method comprising:
receiving, via user input, information about a physical environment proximate to the medical device;
receiving data from one or more sensors of a medical device;
determining a signature signal for the medical device based on the information and the data, wherein the signature signal is a representation of physical attributes of the physical environment proximate to the medical device including:
one or more physical byproducts of the medical device, and
one or more environmental conditions of the physical environment proximate to the medical device;
determining an inverted signal based on the signature signal, wherein the inverted signal is configured to cancel the signature signal; and
generating a physical representation of the inverted signal by one or more electrical or electromechanical components of the medical device,
wherein the physical representation of the inverted signal cancels the physical attributes of the environment represented by the signature signal.

19. The non-transitory, computer-readable medium of claim 18, further including instructions which, when executed by a processor in a computer, cause the computer to perform:
a method, the method comprising:
receiving, via user input, information about a configuration for the medical device; and
wherein the signature signal is further based on the information about the configuration for the medical device.

20. The non-transitory, computer-readable medium of claim 18, further including instructions which, when executed by a processor in a computer, cause the computer to perform:
a method, the method comprising:
receiving additional data from one or more sensors of another medical device; and
wherein the signature signal is further based on the additional data from the one or more sensors of the other medical device.

* * * * *